United States Patent [19]
Bagnoli

[11] Patent Number: 5,880,093
[45] Date of Patent: Mar. 9, 1999

[54] USE OF PARATHORMONE, ITS BIOLOGICALLY ACTIVE FRAGMENTS AND CORRELATED PEPTIDES, FOR THE PREPARATION OF PHARMACEUTICAL COMPOSITIONS USEFUL FOR THE TREATMENT OF PREGNANCY

[76] Inventor: Franco Bagnoli, Via Olanda, 53100 Carpineto (Province of Siena), Italy

[21] Appl. No.: 411,726

[22] PCT Filed: Oct. 8, 1993

[86] PCT No.: PCT/EP93/02755

§ 371 Date: Apr. 5, 1995

§ 102(e) Date: Apr. 5, 1995

[87] PCT Pub. No.: WO94/08613

PCT Pub. Date: Apr. 28, 1994

[30] Foreign Application Priority Data

Oct. 9, 1992 [IT] Italy ................................ MI92A2231

[51] Int. Cl.$^6$ .................................................. A61K 38/00
[52] U.S. Cl. .............................................. 514/12; 514/21
[58] Field of Search ........................................ 514/12, 21

[56] References Cited

PUBLICATIONS

L.S. Mok et al., Endocrine Reviews, vol. 10(4) Nov. 1989, pp. 420–436.

K.L. Shrew et al., Proc. Royal Soc. Exp. Biol. and Med., vol. 175 (4), Apr. 1984, pp. 444–448.

Bernal, et al., Are leukotrienes involved in human uterine contractility?, British J. of Obstetrics and Gynaecology, May 1989, vol. 96, pp. 568–573.

Black, et al., Definition and Antagonism Histamine H$_2$–receptors, Apr. 21, 1972, Nature vol. 236.

Cruz, et al., Effects of Histamine and Serotonin on the Contractility of Isolated Pregnant and Nonpregnant Human Myometrium, 1989, Gynecol Obstet Invest, 28:1–4.

Ballejo, et al., In vitro effects of calcium entry blockers, chlorpromazine and fenoterol upon human pregnant myometrium contractility, 1986, Br. J. Pharm. 89, 515–523.

Calixto et al., Effects Of Compound D600 (Methoxynerapamil) On Drug–Induced Contractions Of Isolated dog Uterine Muscle, 1986, Gen. Pharmac., vol. 17, No. 2, pp. 203–209.

Calixto et al., Ketamine–inhibition of calcium–induced contractions in depolarized rat uterus: a comparison with other calcium antagonists, 1985, Br. J. Pharmac., 85, 189–195.

Sperelakis, et al., Fast Na + channels in smooth muscle from pregnant rat uterus $^{1,2}$, Jun. 1991. Can. J. Physiol. Pharmacol., vol. 70, 1992.

Fuchs, et al., Oxytocin Antagonist (dTVT) and Oxytocin Receptors in Myometrium and Decidua, Apr. 1989, Amer. J. of Perinatology, vol. 6, No. 2.

L.L.S. Mok et al., Parathyroid Hormone As A Smooth Muscle Relaxant, Endocrine Reviews, vol. 10, No. 4, Nov. 1989, pp. 420–436.

R.L. Shew et al., Uterine Relaxing Action Of Parathyroid Hormone: Effect Of Oxidation And Methionine Substitution, Proceedings Of the Society For Experimental Biology and Medicine, vol. 175, No. 4, Apr. 1984, pp. 444–448.

*Primary Examiner*—Cecilia J. Tsang
*Assistant Examiner*—C. Delacroix-Muirheid
*Attorney, Agent, or Firm*—Kenyon & Kenyon

[57] ABSTRACT

Pharmaceutical compositions containing Parathormone as active ingredient, its biologically active fragments and correlated peptides (PTHrP), eventually in combination with appropriate pharmaceutically acceptable additives, useful in the prevention and therapy of abortion and of premature birth and in general for the treatment of pregnancy are described.

16 Claims, 4 Drawing Sheets

USE OF PARATHORMONE, ITS BIOLOGICALLY ACTIVE FRAGMENTS AND CORRELATED PEPTIDES, FOR THE PREPARATION OF PHARMACEUTICAL COMPOSITIONS USEFUL FOR THE TREATMENT OF PREGNANCY

FIELD OF INVENTION

The present invention relates to the use of Parathormone, its biologically active fragments and its correlated peptides (PTHrP) for the prevention and therapy of abortion and of premature birth and in general for the treatment of pregnancy.

BACKGROUND OF THE INVENTION

The generic term Parathormone or parathyroid hormones (commonly indicated by the initials PTH eventually followed by the number of amino acids characterizing the particular fragment) refers to a series of proteins or their fragments which can be found in nature and are assigned to different physiological effects.

Such effects relate principally to the regulation of calcemic homeostasis, favouring the intestinal calcium absorption by the indirect mechanism of hydroxylation of Vitamin D, increasing the re-absorption of calcium in the renal tubules and activating the osteoclasts. More recently it was shown that PTH and PTHrP have a relaxing action on the gastrointestinal muscles and on vascular tissue. Moreover, an increase of hematic flow in the coronaries and a positive chronotropic effect and negative inotropic effect have been demonstrated.

The hormone and its fragments are dosed biologically and the measurement system presently most often used is the USP unit defined as one hundredth of the amount of parathyroid hormone required to increase the calcium contained in 100 ml of normal dog serum by 1 mg within 16–18 hours from administration.

Some studies reported in the literature indicate an in vitro action of parathormone, its fragments and the correlated peptide (PTHrP) on the contractility of rat uterus. According to such studies PTH has an inhibitory action on the contractility of the uterus induced by oxytocin, acetylcholine and prostaglandin.

Literature does not report studies evaluating the action of PTH, its fragments or PTHrP on the contractility of human myometrium, Furthermore, the data reported above cannot suggest results obtainable on the human uterus because the structural and physiological differences between these two tissues do not allow any predictability.

The rat uterus is formed of fiber cells which are completely different from those of the human myometrium. It was, therefore, not possible, according to such studies, to foresee the possibility of using such products in the prevention of abortion and premature birth in humans, since the data obtained in animals cannot be extrapolated to humans. In fact, the smooth muscles (including the human myometrium) do not normally possess fast Na+ channels, while the existence of such channels has been demonstrated in the rat uterus. Sperelakis N. et al., "Fast Na+ channels in smooth muscle from pregnant rat uterus," Can. J. Physiol. Pharmacol. (70) 491–500 (1992). Furthermore, although the concentration of receptors for oxytocin on myometrium membranes is quantitatively similar in human and guinea pig uterus, it was approximately twice that found in rat. Fuchs A. R. et al., "Oxytocin antagonist and oxytocin receptors in myometrium and decidua," Am. J. Perinatol. (6), 205–208 (1989). Moreover, Lopez Bernal A. et al. have confirmed that oxytocin does not contract the nonpregnant human uterus but contracts the non-pregnant rat uterus. Lopez Bernal A. et al., "Are leukotrienes involved in human uterine contractility?" Br. J. Obstet. Gynaecol. (96) 568–573 (1989).

We must also consider the remarkable structural differences of the two organs involved. In fact, the response of a sample of rat uterus is mostly due to the activity of longitudinal muscles while the response of human myometrium strips results from different muscular components. In addition, the behaviour of the two myometriums with respect to histamine is well known. The rat uterus in estrus responds to histamine with an inhibition which is connected to the activation of H2 receptors. Black J. W. et al., "Definition and Antagonism of histamine H2-receptors," Nature (236), 385–390 (1972). The human uterus always reacts with a contraction due to the activation of H1 receptors. Cruz M. et al., "Effects of histamine and serotonin on the contractility of isolated pregnant and nonpregnant human myometrium," Gynecol. Obstet. Invest. (28), 1–4 (1989).

Furthermore, G. Ballejo et al. have demonstrated that the response of the myometrium can depend on the animal species since the sensitivity to calcium in human uterus and in nonpregnant dog uterus did not result to be different, while in the nonpregnant rat myometrium the potency of $CaCl_2$ in inducing contractions in a solution rich of $K^+$ and $Ca^{2+}$ was about 30–40 times higher than that shown in their studies on human myometrium. G. Ballejo et al., "In vitro effects of calcium entry blockers, chlorpromazine and fenoterol upon human pregnant myometrium contractility," Br. J. Pharmacol. (89), 515–523 (1986); Calixto J. B. e Antonio A., "Effects of Compound D600 (methoxyverapamil) on drug-induced-contractions of isolated dog uterine muscle," Gen. Pharmacol. (17), 203–209 (1986); Calixto J. B. and Loch S., "Ketamine inhibition of calcium-induced contractions in depolarized uterus. A comparison with other calcium antagonists," Br. J. Pharmacol. (85). 189–195 (1985). In conclusion, therefore, the effects observed on the human uterus cannot be extrapolated from those obtained on the rat uterus but, rather, the effect noted in vitro on human uterus is surprising.

Figure 1:
FIG. 1 shows the protracted stimulation of contractions induced on human myometrium, by oxytocin (Ox) at a dose of $1 \times 10^{-2}$ U

In the figures the dots (·) indicate the moment of administration of the indicated substance; W (Washing) indicates the washing of the preparation.

DETAILED DESCRIPTION OF THE INVENTION

The present invention relates to the use of Parathormone, its active fragments or correlated peptides for the prevention of abortion and premature birth and in general for the treatment of pregnancy. For the purposes of the present invention the following are particularly indicated: PTH, PTH 1–34. PTH 1–13, PTH 38–64, PTH 67–86, PTHrP.

The compositions can be formulated for intravenous, intramuscular, subcutaneous, rectal and vaginal administration. The types of formulations can be briefly summarized as follows: an injectable pharmaceutical form in which the active ingredient is in the liquid phase or, preferably lyophilized, in the presence eventually of an appropriate stabilizing agent (albumin, peptone, PVP, etc.), an appropriate support (in case of lyophilized product: lactose, mannitol, glycine, etc.) and of a buffer mixture capable of assuring the most appropriate pH for its stability; a rectal pharmaceutical formulation represented by a suppository or preferably a soft gelatine capsule containing the active ingredient suspended in a mixture of water soluble excipients including essentially polyethylene glycols and/or propyleneglycols having the necessary fluidity, with the addition of a polyalcohol such as glycerin and eventually a stabilizing agent (albumin, peptone, PVP, etc. ) and a buffer mixture necessary to maintain the pH in a range of values compatible with PTH and/or its active fragments; a vaginal pharmaceutical formulation such as a vaginal suppository or preferably soft gelatine vaginal ovule containing the active ingredient suspended in a mixture of water soluble excipients essentially similar to that contained in the soft gelatine capsule for rectal use.

The quantity of active ingredient can vary between 100 to 1000 Units, but is preferably between 400 and 800 Units. The following examples describe pharmaceutical formulations containing PTH or its biologically active fragments, which can be used by injection (Examples 1–6), rectal administration (Examples 7–14) and vaginal administration (Examples 15–18). The doses indicated refer to a formulation which can be used for the preparation of 1000 vials, rectal capsules or vaginal capsules.

EXAMPLE 1

| | |
|---|---|
| PTH (or fragment thereof) | 100000 U (USP) |
| Lactose | 10.0 g |
| Phosphate-citrate buffer pH 2.5–3 | 7.5 g |
| Water for injections (USP) q.s. to 1000 ml | |

EXAMPLE 2

| | |
|---|---|
| PTH (or fragment thereof) | 100000 U (USP) |
| Lactose | 10.0 g |
| Human albumin | 20.0 g |
| Phosphate-citrate buffer pH 2.5–3 | 7.5 g |
| Water for injections (USP) q.s. to 1000 ml | |

EXAMPLE 3

| | |
|---|---|
| PTH (or fragment thereof) | 500000 U (USP) |
| Mannitol | 15.0 g |
| PVP | 15.0 g |
| Phosphate-citrate buffer pH 2.5–3 | 7.5 g |
| Water for injections (USP) q.s. to 1000 ml | |

EXAMPLE 4

| | |
|---|---|
| PTH (or fragment thereof) | 750000 U (USP) |
| Glycine | 25.0 g |
| Peptone | 25.0 g |
| Phosphate-citrate buffer pH 2.5–3 | 7.5 g |
| Water for injections (USP) q.s. to 1000 ml | |

EXAMPLE 5

| | |
|---|---|
| PTH (or fragment thereof) | 400000 U (USP) |
| Human albumin | 25.0 g |
| Phosphate-citrate buffer pH 2.5–3 | 7.5 g |
| Water for injections (USP) q.s. to 1000 ml | |

EXAMPLE 6

| | |
|---|---|
| PTH (or fragment thereof) | 400000 U (USP) |
| Lactose | 10.0 g |
| Human albumin | 25.0 g |
| Phosphate-citrate buffer pH 2.5–3 | 7.5 g |
| Water for injections (USP) q.s. to 1000 ml | |

EXAMPLE 7

| | |
|---|---|
| PTH (or fragment thereof) | 500000 U (USP) |
| Human albumin | 20.0 g |
| Phosphate-citrate buffer pH 2.5–3 | 7.5 g |
| Glycerin | 50.0 g |
| Polyethylene glycol 600 | 900.0 g |
| Polyethylene glycol 4000 | 75.0 g |
| Purified Water | 2.0 g |

EXAMPLE 8

| | |
|---|---|
| PTH (or fragment thereof) | 750000 U (USP) |
| Human albumin | 10.0 g |
| Phosphate-citrate buffer pH 2.5–3 | 7.5 g |
| Glycerin | 50.0 g |
| Polyethylene glycol 600 | 900.0 g |
| Polyethylene glycol 4000 | 75.0 g |
| Purified Water | 2.0 g |

EXAMPLE 9

| | |
|---|---|
| PTHrP (or fragment thereof) | 500000 U (USP) |
| Human albumin | 15.0 g |
| Phosphate-citrate buffer pH 2.5–3 | 7.5 g |
| Glycerin | 50.0 g |
| Polyethylene glycol 600 | 900.0 g |
| Polyethylene glycol 4000 | 75.0 g |
| Purified Water | 2.0 g |

EXAMPLE 10

| | |
|---|---|
| PTH (or fragment thereof) | 500000 U (USP) |
| Human albumin | 20.0 g |
| Phosphate-citrate buffer pH 2.5–3 | 7.5 g |
| Glycerin | 40.0 g |

-continued

| | |
|---|---|
| Polyethylene glycol 400 | 250.0 g |
| Polyethylene glycol 200 | 500.0 g |
| Polyethylene glycol 4000 | 100.0 g |
| Sorbitol | 10.0 g |
| Purified Water | 5.0 g |

EXAMPLE 11

| | |
|---|---|
| PTH (or fragment thereof) | 500000 U (USP) |
| Human albumin | 15.0 g |
| Glycerin | 50.0 g |
| Phosphate-citrate buffer pH 2.5–3 | 15.0 g |
| Polyethylene glycol 600 | 900.0 g |
| Polyethylene glycol 4000 | 75.0 g |

EXAMPLE 12

| | |
|---|---|
| PTHrP | 500000 U (USP) |
| Human albumin | 15.0 g |
| Glycerin | 50.0 g |
| Phosphate-citrate buffer pH 2.5–3 | 15.0 g |
| Polyethylene glycol 600 | 900.0 g |
| Polyethylene glycol 4000 | 75.0 g |

EXAMPLE 13

| | |
|---|---|
| PTH (or fragment thereof) | 500000 U (USP) |
| Peptone | 15.0 g |
| Glycerin | 50.0 g |
| Phosphate-citrate buffer pH 2.5–3 | 15.0 g |
| Polyethylene glycol 600 | 900.0 g |
| Polyethylene glycol 4000 | 75.0 g |
| Purified Water | 2.0 g |

EXAMPLE 14

| | |
|---|---|
| PTH (or fragment thereof) | 500000 U (USP) |
| PVP | 15.0 g |
| Glycerin | 50.0 g |
| Phosphate-citrate buffer pH 2.5–3 | 15.0 g |
| Polyethylene glycol 600 | 900.0 g |
| Polyethylene glycol 4000 | 75.0 g |
| Purified Water | 2.0 g |

EXAMPLE 15

| | |
|---|---|
| PTH (or fragment thereof) | 500000 U (USP) |
| Human albumin | 20.0 g |
| Glycerin | 80.0 g |
| Phosphate-citrate buffer pH 2.5–3 | 25.0 g |
| Polyethylene glycol 600 | 2500.0 g |
| Polyethylene glycol 4000 | 300.0 g |
| Purified Water | 2.0 g |

EXAMPLE 16

| | |
|---|---|
| PTHrP | 500000 U (USP) |
| Human albumin | 20.0 g |
| Glycerin | 80.0 g |
| Phosphate-citrate buffer pH 2.5–3 | 15.0 g |
| Polyethylene glycol 600 | 2500.0 g |
| Polyethylene glycol 4000 | 300.0 g |
| Purified Water | 2.0 g |

EXAMPLE 17

| | |
|---|---|
| PTH (or fragment thereof) | 500000 U (USP) |
| Peptone | 25.0 g |
| Glycerin | 80.0 g |
| Phosphate-citrate buffer pH 2.5–3 | 25.0 g |
| Polyethylene glycol 600 | 2500.0 g |
| Polyethylene glycol 4000 | 300.0 g |
| Purified Water | 2.0 g |

EXAMPLE 18

| | |
|---|---|
| PTH (or fragment thereof) | 500000 U (USP) |
| PVP | 25.0 g |
| Glycerin | 80.0 g |
| Phosphate-citrate buffer pH 2.5–3 | 25.0 g |
| Polyethylene glycol 600 | 2500.0 g |
| Polyethylene glycol 4000 | 300.0 g |
| Purified Water | 2.0 g |

Figure 2:
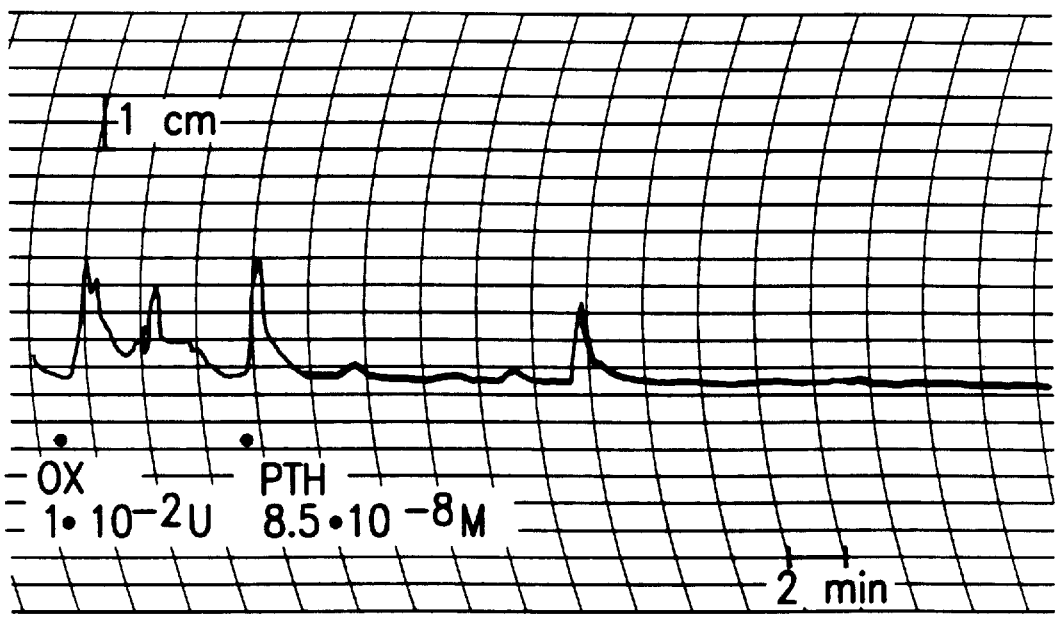
FIG. 2 shows the inhibitory effect (flat trace) induced by intact human parathormone at a dose of $8.5 \times 10^{-8}$M on human myometrium stimulated with oxytocin at a dose of $1 \times 10^{-2}$ U.

Experimental Trials on the in vitro motility of fragments of myometrium of pregnant women By using "in vitro" fragments of myometrium taken during Caesarean birth according to the technique described in "IL FARMACO", Edizione Scientifica, 31: pages 329–336 (1976), a net inhibitory effect on contraction induced by oxytocyn has been observed, as can be seen in FIGS. 1 and 2 attached. In FIG. 2 there is a net inhibitory effect, indicated in the flat trace, induced by intact human Parathormone (PTH) at a dose of $8.5 \times 10^{-8}$M, on human myometrium stimulated with oxytocyn at a dose of $1 \times 10^{-2}$ U. The inhibitory effect induced by PTH is particularly evident when compared with the protracted stimulation of contractions induced by oxytocyn (Ox) at a dose of $1 \times 10^{-2}$ U (FIG. 1).

Figure 3:
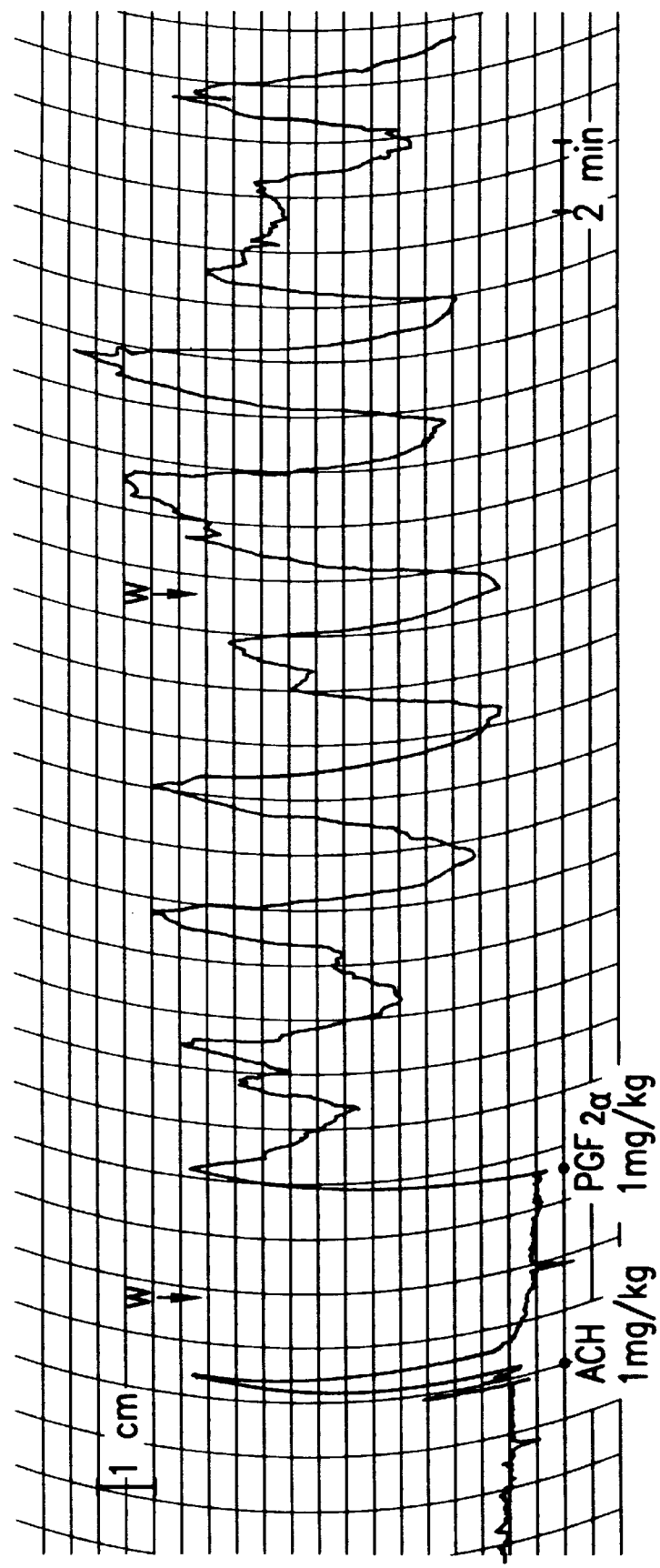
FIG. 3 shows typical contractions induced by $PGF^2$alpha (1 mg/kg) indicating intensity and duration.
Figure 4:
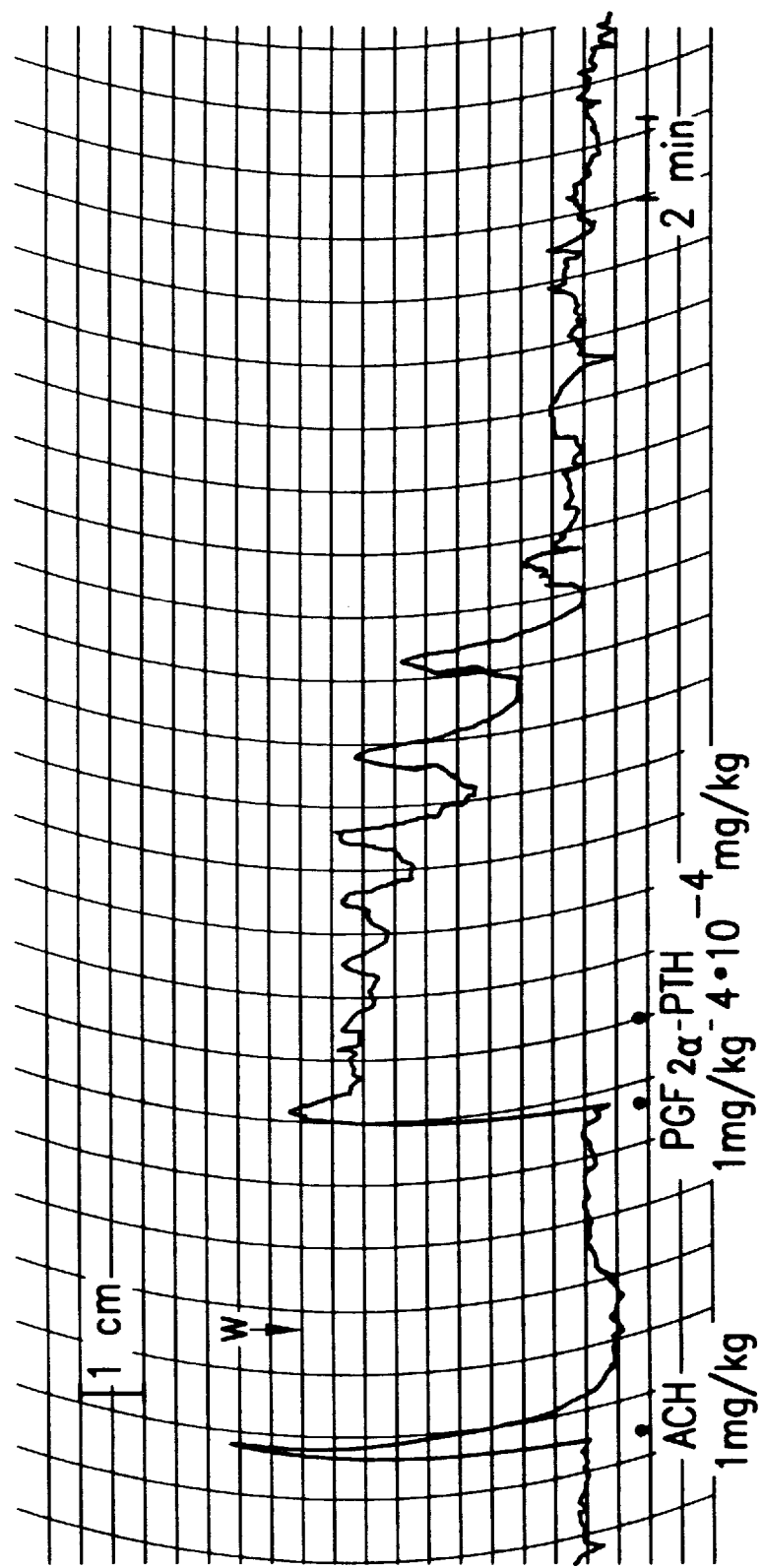
FIG. 4 shows the response at the same dosage as in FIG. 3 after administration of intact human PTH at a dose of $4 \times 10^{-4}$ mg/kg.

Furthermore. Parathormone, has also been essayed for the contractions induced by PGF2alpha according to the technique described in the British Journal of Pharmacology 93: 185–191 (1988). FIG. 3 shows a typical contraction induced by PGF2alpha (1 mg/kg) indicating intensity and duration. If we compare the same response at the same dosage on FIG. 4 we can see a clear inhibitory effect both in terms of intensity and duration as a result of administration of whole human PTH at a dose of $4 \times 10^{-4}$ mg/Kg.

In the graphs the dots (·) indicate the moment of administration of the substance indicated. The letter W (Washing) indicates the washing of the preparation.

Experimental clinical effects

Three pregnant women having symptoms indicating the likelihood of premature birth have been observed while in their 34–36th week of pregnancy. The patients underwent a cardiotocography which showed waves revealing uterine contractions. Arterial pressure, heart rate and skin coloring were evaluated. The women were clearly aware of the contractions and of the pain caused by such contractions.

The women were administered 100 Units of synthetic Parathormone 1–34 (two vials according to Examples 1 and 2) by rapid infusion (10 minutes), diluted in 200 cc of physiological solution. Two blood samples were taken before and after infusion and the serum was frozen and stored at −20° C. for the evaluation of the mineral elements (calcium, phosphorous, magnesium, alkaline phosphatase, parathormone, progesterone, estradiol). The results have shown the efficacy of Parathormone on uterine contractility while no side effects have been noted either in the mother or the fetus.

Figure 5:
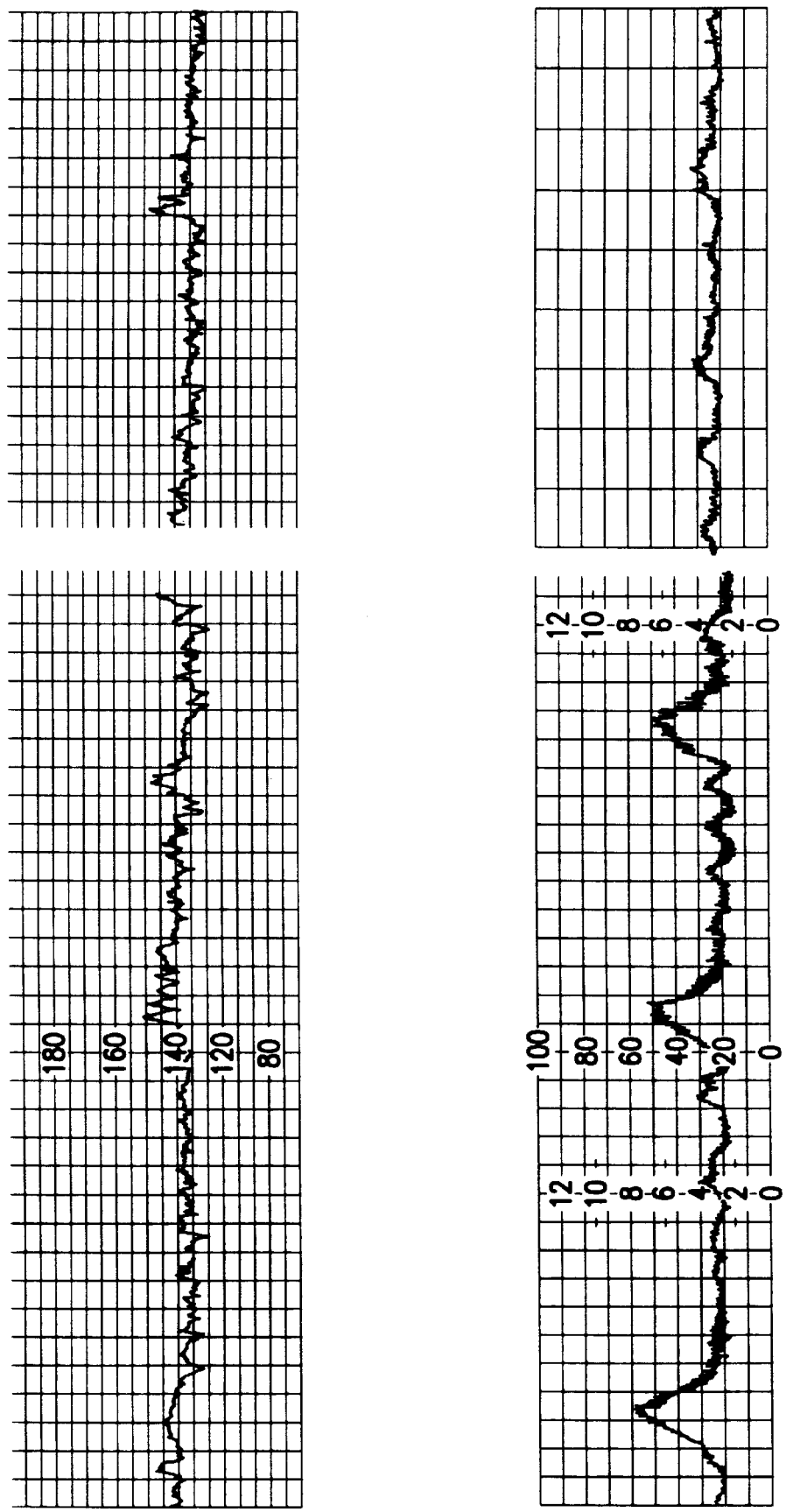
FIG. 5 reports on the left side the basal value of uterine contractility and fetal heart rate in a pregnant woman; the same parameters after 10 infusion with PTH 200 U are reported on the right side.

In particular, the cardiotocography has shown the disappearance of waves referring to uterine contractions during the period of monitoring (40 minutes); the fetal heart beat did not show variations and remained within the normal limits (FIG. 5). The patients indicated the immediate disappearance of uterine contractions and of pain caused by the same contractions, particularly in the lumbar-sacral region and reported also a feeling of well-being and decreased abdominal weight. The arterial pressure and heart rate did not show variations of worthwhile note and no side effects were noted in relation to the infusion of the drug.

I claim:

1. A method for preventing premature birth or spontaneous abortion comprising administering to a pregnant human patient in need thereof a composition comprising a therapeutically effective amount of parathormone, PTHrP or a biologically active fragment of parathormone.

2. The method of claim 1 wherein the parathormone, PTHrP or biologically active fragment of parathormone is selected from the group consisting of PTH, PTH 1–34, PTH 1–13, PTH 38–64, PTH 67–86 and PTHrP.

3. The method of claim 1 wherein parathormone is administered to the patient.

4. The method of claim 1 wherein the composition further comprises a pharmaceutically acceptable carrier.

5. The method of claim 1 wherein the composition is administered intravenously, intramuscularly, subcutaneously, rectally or vaginally.

6. The method of claim 1 wherein the composition comprises from about 100 to about 1000 U (USP) of parathormone, PTHrP or a biologically active fragment of parathormone.

7. The method of claim 1 wherein the composition comprises from about 400 to about 800 U (USP) parathormone, PTHrP or a biologically active fragment of parathormone.

8. A method for treating unwanted uterine contractions in a pregnant human patient comprising administering to said patient a pharmaceutical composition comprising a therapeutically effective amount of parathormone, PHTrP or a fragment of parathormone having human myometrium regulating activity.

9. The method of claim 8 wherein the parathormone, PTHrP or biologically active fragment of parathormone is selected from the group consisting of PTH, PTH 1–34, PTH 1–13, PTH 38–64, PTH 67–86 and PTHrP.

10. The method of claim 8 wherein parathormone is administered to the patient.

11. The method of claim 8 wherein the composition further comprises a pharmaceutically acceptable carrier.

12. The method of claim 8 wherein the composition is administered intravenously, intramuscularly, subcutaneously, rectally or vaginally.

13. The method of claim 8 wherein the composition comprises from about 100 to about 1000 U (USP) of parathormone, PTHrP or a biologically active fragment of parathormone.

14. The method of claim 8 wherein the composition comprises from about 400 to about 800 U (USP) parathormone, PTHrP or a biologically active fragment of parahormone.

15. A pharmaceutical composition for preventing premature birth, spontaneous abortion or treating unwanted uterine contractions consisting essentially of from about 100 to about 1000 U (USP) of parathormone, PTHrP or biologically active fragment of parathormone.

16. The composition of claim 15 consisting essentially of from about 400 to about 800 U (USP) parathormone, PTHrP or a biologically active fragment of parathormone.

* * * * *

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 84 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 1:

```
Ser Val Ser Glu Ile Gln Leu Met His Asn Leu Gly Lys His Leu Asn
                  5                  10                          15
Ser Met Glu Arg Val Glu Trp Leu Arg Lys Lys Leu Gln Asp Val His
             20                      25                  30
Asn Phe Val Ala Leu Gly Ala Pro Leu Ala Pro Arg Asp Ala Gly Ser
         35                  40                  45
Gln Arg Pro Arg Lys Lys Glu Asp Asn Val Leu Val Glu Ser His Glu
     50                      55                  60
Lys Ser Leu Gly Glu Ala Asp Lys Ala Asp Val Asp Val Leu Thr Lys
 65                  70                      75                  80
Ala Lys Ser Gln
```

( 2 ) INFORMATION FOR SEQ ID NO: 2:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 2:

```
Ser Val Ser Glu Ile Gln Leu Met His Asn Leu Gly Lys His Leu Asn
                  5                  10                          15
Ser Met Glu Arg Val Glu Trp Leu Arg Lys Lys Leu Gln Asp Val His
             20                      25                  30
Asn Phe
```

( 2 ) INFORMATION FOR SEQ ID NO: 3:

(i) SEQUENCE CHARACTERISTICS:
- (A) LENGTH: 13 amino acids
- (B) TYPE: amino acid
- (C) STRANDEDNESS: single
- (D) TOPOLOGY: linear (ii) MOLECULE TYPE: protein (xi) SEQUENCE DESCRIPTION: SEQ ID NO: 3:

Ser Val Ser Glu Ile Gln Leu Met His Asn Leu Gly Lys
                5                   10

(2) INFORMATION FOR SEQ ID NO: 4:

(i) SEQUENCE CHARACTERISTICS:
- (A) LENGTH: 20 amino acids
- (B) TYPE: amino acid
- (C) STRANDEDNESS: single
- (D) TOPOLOGY: linear (ii) MOLECULE TYPE: protein (xi) SEQUENCE DESCRIPTION: SEQ ID NO: 4:

Tyr Leu Thr Gln Glu Thr Asn Lys Val Glu Thr Tyr Lys Glu Gln Pro
                5                   10                  15
Leu Lys Thr Pro
            20

(2) INFORMATION FOR SEQ ID NO: 5:

(i) SEQUENCE CHARACTERISTICS:
- (A) LENGTH: 141 amino acids
- (B) TYPE: amino acid
- (C) STRANDEDNESS: single
- (D) TOPOLOGY: linear (ii) MOLECULE TYPE: protein (xi) SEQUENCE DESCRIPTION: SEQ ID NO: 5:

Ala Val Ser Glu His Gln Leu Leu His Asp Lys Gly Lys Ser Ile Gln
                5                   10                  15
Asp Leu Arg Arg Arg Phe Phe Leu His His Leu Ile Ala Glu Ile His
                20                  25                  30
Thr Ala Glu Ile Arg Ala Thr Ser Glu Val Ser Pro Asn Ser Lys Pro
            35                  40                  45
Ser Pro Asn Thr Lys Asn His Pro Val Arg Phe Gly Ser Asp Asp Glu
    50                  55                  60
Gly Arg Tyr Leu Thr Gln Glu Thr Asn Lys Val Glu Thr Tyr Lys Glu
65                  70                  75                  80
Gln Pro Leu Lys Thr Pro Gly Lys Lys Lys Lys Gly Lys Pro Gly Lys
                85                  90                  95
Arg Lys Glu Gln Glu Lys Lys Lys Arg Arg Thr Arg Ser Ala Trp Leu
            100                 105                 110
Asp Ser Gly Val Thr Gly Ser Gly Leu Glu Gly Asp His Leu Ser Asp
            115                 120                 125
Thr Ser Thr Thr Ser Leu Glu Leu Asp Ser Arg Arg His
    130                 135                 140